United States Patent [19]

Gottschalk et al.

[11] Patent Number: 4,772,541
[45] Date of Patent: Sep. 20, 1988

[54] PHOTOHARDENABLE COMPOSITIONS CONTAINING A DYE BORATE COMPLEX AND PHOTOSENSITIVE MATERIALS EMPLOYING THE SAME

[75] Inventors: Peter Gottschalk, Centerville, Ohio; Gary B. Schuster, Champaign, Ill.

[73] Assignee: The Mead Corporation, Dayton, Ohio

[21] Appl. No.: 917,873

[22] Filed: Oct. 10, 1986

Related U.S. Application Data

[63] Continuation-in-part of Ser. No. 800,014, Nov. 20, 1985, abandoned.

[51] Int. Cl.$^4$ .................. G03C 1/72; G03C 1/00; G03C 1/727; G03C 5/00
[52] U.S. Cl. ............................ 430/339; 430/170; 430/281; 430/314; 430/495; 430/341; 430/914; 430/916; 430/927
[58] Field of Search ............... 430/138, 170, 281, 314, 430/914, 916, 927, 341

[56] References Cited

U.S. PATENT DOCUMENTS

| | | | |
|---|---|---|---|
| 2,850,445 | 9/1958 | Oster | 204/158 |
| 2,875,047 | 2/1959 | Oster | 96/35 |
| 3,495,987 | 2/1970 | Moore | 96/115 |
| 3,547,633 | 12/1970 | Rust | 96/45.2 |
| 3,567,453 | 3/1971 | Borden | 96/91 |
| 3,579,339 | 5/1971 | Chang et al. | 96/74 |
| 3,615,452 | 10/1971 | Cerwonka | 96/35.1 |
| 3,627,656 | 12/1987 | Millter et al. | 204/159.24 |
| 3,716,366 | 2/1973 | Riester | 430/338 |
| 4,297,441 | 10/1981 | Kaneko et al. | 430/566 X |
| 4,307,182 | 12/1981 | Dalzell et al. | 430/339 |
| 4,343,891 | 8/1982 | Aasen et al. | 430/337 |
| 4,399,209 | 8/1983 | Sanders et al. | 430/138 |
| 4,447,521 | 5/1984 | Tiers et al. | 430/337 |
| 4,450,227 | 5/1984 | Holmes et al. | 430/339 |
| 4,562,137 | 12/1985 | Sanders | 430/138 |
| 4,754,921 | 8/1973 | Riester | 430/338 |

FOREIGN PATENT DOCUMENTS

| | | |
|---|---|---|
| 147424 | 4/1981 | Fed. Rep. of Germany . |
| 1370060 | 10/1974 | United Kingdom . |
| 1370059 | 10/1974 | United Kingdom . |
| 1370058 | 10/1974 | United Kingdom . |

OTHER PUBLICATIONS

Color Print Systems Based on Dispersion Photopolymerization, *Photographic Science and Engineering*, vol. 13, No. 2, Mar.–Apr. 1969.

*Primary Examiner*—Mukund J. Shah
*Attorney, Agent, or Firm*—Smith & Schnacke

[57] ABSTRACT

A photohardenable composition comprising a free radical addition polymerizable or crosslinkable compound and a cationic dye-borate anion complex, said complex being capable of absorbing actinic radiation and producing free radicals which initiate free radical polymerization or crosslinking of said compound; and photosensitive materials employing the composition where in one embodiment the composition is microencapsulated.

12 Claims, No Drawings

PHOTOHARDENABLE COMPOSITIONS CONTAINING A DYE BORATE COMPLEX AND PHOTOSENSITIVE MATERIALS EMPLOYING THE SAME

CROSS-REFERENCE TO RELATED APPLICATION

This application is a continuation-in-part of U.S. application Ser. No. 800,014 filed Nov. 20, 1985, now abandoned.

BACKGROUND OF THE INVENTION

The present invention relates to novel photohardenable compositions and to photosensitive materials employing them. More particularly, it relates to free radical addition polymerizable compositions containing a cationic dye-borate anion complex as a photoinitiator.

U.S. Pat. Nos. 4,399,209 and 4,440,846 to The Mead Corporation describe imaging materials and imaging processes in which images are formed through exposure-controlled release of an image-forming agent from a micro-capsule containing a photohardenable composition. The imaging material is exposed image-wise to actinic radiation and the microcapsules are subjected to a uniform rupturing force. Typically the image-forming agent is a color precursor which is released image-wise from the microcapsules to a developer sheet whereupon it reacts with a developer to form a visible image.

Full color imaging materials include a photosensitive layer which contains three sets of microcapsules. Each set of microcapsules is sensitive to a different band of radiation in the ultraviolet or blue spectrum and contains a cyan, magenta or yellow image-forming agent. One of the problems which has been encountered in designing commercially acceptable full color imaging materials employing these techniques has been the relatively narrow wavelength band over which most photohardenable compositions are sensitive to actinic radiation. In most cases, the compositions are only sensitive to ultraviolet radiation or blue light, e.g., 350 to 480 nm. Furthermore, the absorption spectra of the initiators employed in these microcapsules are never perfectly distinct. There is always a degree of overlap in the absorption curves and sometimes it is substantial. Exposure conditions therefore must be controlled carefully to avoid cross-exposure.

It would be desirable to extend the sensitivity of the photohardenable compositions used in these imaging materials to longer wavelengths. By extending the sensitivity of the photohardenable compositions to longer wavelengths, the absorption bands of the initiators can be separated and the amount of overlap in the absorption spectra of the initiators and the concomitant incidence of cross-exposure can be reduced. It would be particularly desirable if compositions could be designed with sensitivities to selected wavelength bands throughout the visible spectrum (400 to 700 nm) since this would provide a visible light-sensitive material which could be exposed directly by reflection or transmission imaging and without the need for image processing to translate the image into three wavelengths of ultravoilet or blue radiation.

Visible light-sensitive, dye-sensitized photopolymerizable compositions are known in the art. A survey of these systems is provided by Eaton, David E., "Dye Sensitized Photopolymerization", *Advances in Photochemistry*, Vol. 13, pp 427-87 (1985). In their simplest form these compositions include a photopolymerizable vinyl compound, a photoreducible or photooxidizable dye and an activator which functions as a reducing agent or an oxidizing agent for the dye. The dyes are excited by light to a triplet state which reacts with the reducing agent or oxidizing agent to yield radicals which can initiate polymerizations. There are a number of examples of dyesensitized photopolymerizable compositions in the patent literature. See Oster, U.S. Pat. Nos. 2,850,445 and 2,875,047 (Rose Bengal with hydrazine or thiourea); 3,547,633 (quinoidal family dyes with triorganophosphines, triorganoarsenines or sulfinic acid derivatives); 3,615,452 (phenazine or oxazine dyes and diazonium salts); 3,627,656 (phenothiazine dyes and sulfinic compounds); 3,485,987 (cyanine dyes and bromine donors) and 3,488,269 (thionine dyes and methylenes or methines).

U.S. Pat. No. 3,579,339 describes panchromatic imaging systems in which a dye-sensitized photopolymerizable composition containing a color coupler of the type used in silver halide color films is dispersed in a binder such as gelatin and coated on a support to provide a photosensitive layer having small, dye-sensitized, photopolymerizable droplets therein. Exposure to light polymerizes the composition and reduces the permeability of the droplets to a liquid color developer such that application of the color developer differentially produces color in the unexposed or underexposed droplets. Three photopolymerizable dispersions are provided on a support in three separate layers. One layer contains a yellow color former and is sensitive to blue light, the second layer contains a magenta color former and is sensitive to green light and the third contains a cyan color former and is sensitive to red light. Exposure to visible light selectively hardens the droplets such that, upon application of a developer, cyan, magenta and yellow positive images are formed in the respective layers. These systems are described in more detail in Chang et al, "Color Print Systems Based on Dispersion Photopolymerization", *Photographic Science and Engineering*, Vol. 13, No. 2, pp. 84-9 (1969).

SUMMARY OF THE INVENTION

It has been found that cationic dye-borate anion complexes are useful photoinitiators of free radical addition reactions. The mechanism whereby the complexes absorb energy and generate free radicals is not entirely clear, however, cyanine and similar dyes which are useful in the complex, are known to form little or no triplet state. It is, therefore, believed that upon exposure to actinic radiation, the dye in the complex is excited to a singlet state in which it accepts an electron from the borate anion as follows:

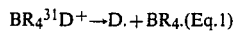

$$BR_4{}^{31}D^+ \rightarrow D \cdot + BR_4 \cdot \quad (Eq. 1)$$

The lifetime of the dye singlet state is extremely short by comparison to the lifetime of the triplet state of a conventional photoinitiator indicating that the complex provides a very efficient electron transfer. In solution in the polymerizable compound, ionic pairing of the borate anion and the cationic dye is believed to provide favorable spacial distribution for promoting electron transfer to such an extent that the transfer occurs even though the lifetime of the singlet state is very short. After electron transfer, the borate anion reacts by a mechanism which is not clear to form a radical which initiates free radical addition polymerization or crosslinking of the polymerizable or crosslinkable species in the photohardenable composition (see Eq. 2 below).

In most prior dye-sensitized systems, random collisions of the dye and the corresponding activator (i.e., oxidizing or reducing agent) are relied upon to effect the electron transfer. In some cases these collisions produce a complex also known as an exciplex. The complex is a transient entity and its formation and electron transfer are controlled by diffusion. The complexes used in the present invention are pre-formed (not diffusion controlled) and, therefore, provide higher film speeds than have been available in many prior art systems.

Thus, the present invention is believed to provide a means for generating free radicals from the singlet state of an excited dye and, insodoing, provides photohardenable compositions which are sensitive at longer wavelengths.

One of the particular advantages of using cationic dye-borate anion complexes as initiators of free radical addition reactions is the ability to select from a large number of dyes which absorb at substantially different wavelengths. The absorption characteristics of the complex are principally determined by the dye. Thus, by selecting a dye which absorbs at 400 nm or greater, the sensitivity of the photosensitive material can be extended well into the visible range. The cationic dye-borate anion complex sensitized compositions are particularly useful in providing full color photosensitive materials. In these materials, a layer including three sets of microcapsules having distinct sensitivity characteristics is provided on a support. Each set of microcapsules respectively contains a cyan, magenta, and yellow color-forming agent. Complexes can be designed for use in the cyan-, magenta-, and yellow-forming capsules which are respectively sensitive to red, green and blue light.

Photosensitive materials useful in providing full color images are described in U.S. application Ser. No. 339,917, filed January 18, 1982, and U.S. Pat. No. 4,576,891. The absorption characteristics of the three sets of microcapsules in these photosensitive materials must be sufficiently different that the cyan-forming capsules can be differentially hardened at a predetermined wavelength or over a predetermined wavelength band without hardening the magenta or yellow-forming capsules and, likewise, sufficiently different that the magenta-forming and yellow-forming capsules can be selectively hardened upon exposure respectively to second and third wavelengths or wavelength bands, without hardening the cyan-forming capsules or hardening the other of the yellow-forming or magenta-forming capsules. Microcapsules having this characteristic (i.e., cyan-, magenta and yellow-forming capsules which can be selectively hardened by exposure at distinct wavelengths without cross-exposure) are referred to herein as having "distinctly different sensitivities."

As indicated above, because most photohardenable compositions are sensitive to ultraviolet radiation or blue light and they tend not to be sensitive to wavelengths greater than about 480 nm, it has been difficult to achieve microcapsules having distinct sensitivities at three wavelengths. Often it can only be achieved by carefully adjusting the exposure amounts so as to not cross-expose the capsules.

In its simplest form, the present invention facilitates the achievement of distinct sensitivities by shifting the peak absorption of the initiators in at least one of the microcapsules to higher wavelengths, such as wavelengths greater than about 500 nm through the use of a dye borate complex. In this manner, instead of attempting to establish distinct sensitivities at three wavelengths within the narrow wavelength range of, for example, 350 nm to 480 nm, sensitivity can be established over a broader range of, for example, 350 to 550 nm or higher. In accordance with the more preferred embodiments of the invention, the sensitivity of the microcapsules is extended well into the visible spectrum to 600 nm and in some cases to about 700 nm. In its more complex form, the present invention provides a full color imaging sheet in which the microcapsules are sensitive to red, green and blue light.

A principal object of the present invention is to provide photohardenable compositions which are sensitive to visible light, e.g., wavelengths greater than about 500 nm.

A further object of the present invention is to provide visible light-sensitive, dye complex sensitized, photohardenable compositions which are useful in the imaging materials described in U.S. Pat. Nos. 4,399,209 and 4,440,846 and in other applications.

A more particular object of the present invention is to provide an imaging material of the type described in U.S. Pat. Nos. 4,399,209 and 4,440,846 which is sensitive to red, green and blue light through the use of dye borate complexes.

Another object of the present invention is to provide photohardenable compositions which are sensitive at greater than about 400 nm and which are useful as photoresists or in forming polymer images.

These and other objects are accomplished in accordance with the present invention which, in one embodiment, provides:

A photohardenable composition comprising a free radical addition polymerizable or crosslinkable compound and a cationic dye-borate anion complex, said complex being capable of absorbing actinic radiation and producing free radicals which initiate free radical addition polymerization or crosslinking of said addition polymerizable or crosslinkable compound.

Another embodiment of the present invention resides in a photosensitive material comprising a support having a layer of photosensitive microcapsules on the surface thereof, at least a portion of said microcapsules containing an internal phase including a photohardenable composition comprising a free radical addition polymerizable or crosslinkable compound and a cationic dye-borate anion complex.

Still another embodiment of the present invention resides in a photosensitive material useful in forming full color images comprising a support having a layer of photosensitive microcapsules on the surface thereof, said photosensitive microcapsules comprising a first set of microcapsules having a cyan image-forming agent associated therewith, a second set of microcapsules having a magenta image-forming agent associated therewith, and a third set of microcapsules having a yellow image-forming agent associated therewith, at least one of said first, second, and third sets of microcapsules containing an internal phase which includes a photohardenable composition including a free radical addition polymerizable or cross-linkable compound and a cationic dye-borate anion complex.

A further embodiment of the present invention resides in a photosensitive material comprising a support having a layer of a photohardenable composition on the surface thereof, said photohardenable composition comprising a free radical addition polymerizable or crosslinkable compound and a cationic dye-borate anion complex.

Definition

The term "complex" as used herein refers to complexes of the formula (I) below which may be a simplification of their structure. The term and formula also include complexes in which a cluster of two or more dye cations may be complexed with two or more borate anions.

The term "cationic dye" includes dyes such as cyanine dyes as well as dyes in which a cationic moiety such as a quaternary ammonium ion is covalently linked to an otherwise neutral dye structure by a linking group.

U.S. Pat. Nos. 4,399,209 and 4,440,846 and U.S. application Ser. Nos. 339,917, filed Jan. 18, 1982, and 620,994, filed June 15, 1984, are incorporated herein by reference to the extent that reference thereto may be necessary to complete this disclosure.

Cationic dye-borate anion complexes are known in the art. Their preparation and use in imaging systems is described in U.S. Pat. Nos. 3,567,453; 4,307,182; 4,343,891; 4,447,521; and 4,450,227. The complexes used in the present invention can be represented by the general formula (I):

$$\begin{array}{c} R^1 \\ \diagdown \\ R^2 \end{array} B^- \begin{array}{c} R^4 \\ \diagup \\ R^3 \end{array} \quad D^+ \quad (I)$$

where $D^+$ is a cationic dye; and $R^1$, $R^2$, $R^3$, and $R^4$ are independently selected from the group consisting of alkyl, aryl, alkaryl, allyl, aralkyl, alkenyl, alkynyl, alicyclic and saturated or unsaturated heterocyclic groups.

Useful dyes form photoreducible but dark stable complexes with borate anions and can be cationic methine, polymethine, triarylmethane, indoline, thiazine, xanthene, oxazine and acridine dyes. More specifically, the dyes may be cationic cyanine, carbocyanine, hemicyanine, rhodamine and azomethine dyes. In addition to being cationic, the dyes should not contain groups which would neutralize or desensitize the complex or render the complex poorly dark stable. Examples of groups which generally should not be present in the dye are acid groups such as free carboxylic or sulphonic acid groups.

Specific examples of useful cationic dyes are Methylene Blue, Safranine O Malachite Green, cyanine dyes of the general formula (II) and rhodamine dyes of the formula (III):

(II)

n=0, 1, 2, 3,
R=alkyl
Y=CH=CH, N-CH$_3$, C(CH$_3$)$_2$, O, S, Se (III)

R', R=alkyl, aryl, and any combination thereof

While they have not been tested, the cationic cyanine dyes disclosed in U.S. Pat. No. 3,495,987 should be useful in the present invention.

The borate anion is designed such that the borate radical generated upon exposure to light and after electron transfer to the dye (Eq. 1) readily dissociates with the formation of a radical as follows:

$$BR_4 \cdot \rightarrow BR_3 + R \cdot \quad (Eq.\ 2)$$

For example particularly preferred anions are triphenylbutylborate and trianisylbutylborate anions because they readily dissociate to triphenylborane or trianisylborane and a butyl radical. On the other hand tetrabutylborate anion does not work well presumably because the tetrabutylborate radical is not stable and it readily accepts an electron back from the dye in a back electron transfer and does not dissociate efficiently. Likewise, tetraphenylborate anion is very poor because the phenyl radical is not easily formed.

Preferably, at least one but not more than three of $R^1$, $R^2$, $R^3$, and $R^4$ is an alkyl group. Each of $R^1$, $R^2$, $R^3$, and $R^4$ can contain up to 20 carbon atoms, and they typically contain 1 to 7 carbon atoms. More preferably $R^1$–$R^4$ are a combination of alkyl group(s) and aryl group(s) or aralkyl group(s) and still more preferably a combination of three aryl groups and one alkyl group.

Representative examples of alkyl groups represented by $R^1$–$R^4$ are methyl, ethyl, propyl, butyl, pentyl, hexyl, octyl, stearyl, etc. The alkyl groups may be substituted, for example, by one or more halogen, cyano, acyloxy, acyl, alkoxy or hydroxy groups.

Representative examples of aryl groups represented by $R^1$–$R^4$ include phenyl, naphthyl and substituted aryl groups such as anisyl and alkaryl such as methylphenyl, dimethylphenyl, etc. Representative examples of aralkyl groups represented by $R^1$–$R^4$ groups include benzyl. Representative alicyclic groups include cyclobutyl, cyclopentyl, and cyclohexyl groups. Examples of an alkynyl group are propynyl and ethynyl, and examples of alkenyl groups include a vinyl group.

As a general rule, useful cationic dye-borate anion complexes must be identified empirically, however, potentially useful cationic dye and borate anion combinations can be identified by reference to the Weller equation (Rehm, D. and Weller, A., *Isr. J Chem.* (1970), 8, 259–271), which can be simplified as follows.

$$\Delta G = E_{ox} - E_{red} - E_{h\nu} \quad (Eq.\ 3)$$

where $\Delta G$ is the change in the Gibbs free energy, $E_{ox}$ is the oxidation potential of the borate anion $BR_4^-$, $E_{red}$ is the reduction potential of the cationic dye, and $E_{h\nu}$ is the energy of light used to excite the dye. Useful complexes will have a negative free energy change. Similarly, the difference between the reduction potential of the dye and the oxidation potential of the borate must be negative for the complex to be dark stable, i.e., Eox-Ered>O.

As indicated, Eq. 3 is a simplification and it does not absolutely predict whether a complex will be useful in the present invention or not. There are a number of other factors which will influence this determination. One such factor is the effect of the monomer on the complex. It is also known that if the Weller equation produces too negative a value, deviations from the equation are possible. Furthermore, the Weller equation only predicts electron transfer, it does not predict whether a particular dye complex is an efficient initiator of polymerization. The equation is a useful first approximation.

Specific examples of cationic dye-borate anion complexes useful in the present invention are shown in the following table with their λ max.

TABLE

| Complex No. | Structure | λmax (TMPTA) |
|---|---|---|
| 1. | [benzothiazole dimer with CH$_3$ bridge, N-CH$_2$CH$_3$ groups] Ph$_3$B$^\ominus$n-C$_4$H$_9$ | 552 nm |
| 2. | [benzothiazole dimer, N-C$_7$H$_{15}$ groups] Ph$_3$B$^\ominus$n-C$_4$H$_9$ | 568 nm |
| 3. | [benzoxazole dimer, N-n-C$_6$H$_{13}$ groups] Ph$_3$B$^\ominus$n-C$_4$H$_9$ | 492 nm |
| 4. | [benzothiazole dimer, N-CH$_3$ groups] Ph$_3$B$^\ominus$n-C$_4$H$_9$ | 428 nm |
| 5. | [phenothiazine-type with (CH$_3$)N and N(CH$_3$)$_2$, S$_\oplus$] Ph$_3$B$^\ominus$n-C$_4$H$_9$ | 658 nm |
| 6. | [phenazine-type with CH$_3$, NH$_2$ groups and N-phenyl] Ph$_3$B$^\ominus$n-C$_4$H$_9$ | 528 nm |
| 7. | [dye with S, N-CH$_2$CH$_3$ groups] Ar$_3$B$^\ominus$—R' | 450 nm |

| No. | R' | Ar |
|---|---|---|
| 7A | n-butyl | phenyl |
| 7B | n-hexyl | phenyl |
| 7C | n-butyl | anisyl |

8. 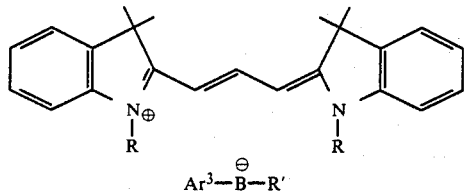   550 nm $Ar_3\overset{\ominus}{-}B-R'$

| No. | R | R' | Ar |
|---|---|---|---|
| 8A | methyl | n-butyl | phenyl |
| 8B | methyl | n-hexyl | phenyl |
| 8C | n-butyl | n-butyl | phenyl |
| 8D | n-butyl | n-hexyl | phenyl |
| 8E | n-heptyl | n-butyl | phenyl |
| 8F | n-heptyl | n-hexyl | phenyl |
| 8G | ethyl | n-butyl | phenyl |

9. 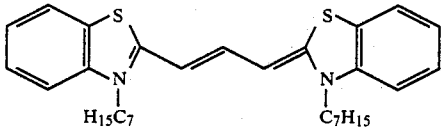   570 System

+

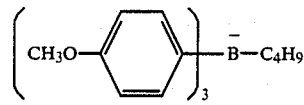

10. 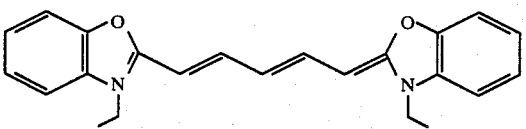   590 System

+

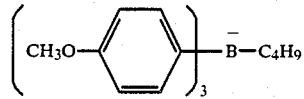

11. 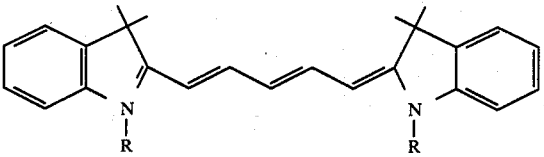   640 nm

+

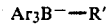

$Ar_3B^- - R'$

| No. | R | R' | Ar |
|---|---|---|---|
| 11A | methyl | n-butyl | phenyl |
| 11B | methyl | n-hexyl | phenyl |
| 11C | n-butyl | n-butyl | phenyl |
| 11D | n-butyl | n-hexyl | phenyl |
| 11E | n-phenyl | n-butyl | phenyl |
| 11F | n-pentyl | n-hexyl | phenyl |
| 11G | n-heptyl | n-butyl | phenyl |
| 11H | n-heptyl | n-hexyl | phenyl |
| 11I | methyl | n-butyl | anisyl |

TABLE-continued

| Complex No. | Structure | λmax (TMPTA) |
|---|---|---|
| 12. | 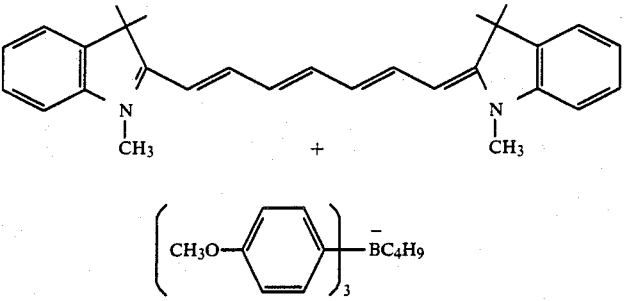 | 740 System |

The cationic dye-borate anion complexes can be prepared by reacting a borate salt with a dye in a counter-ion exchange in a known manner. See Hishiki, Y., *Repts. Sci. Research Inst.* (1953), 29, pp 72–79. Useful borate salts are sodium salts such as sodium tetraphenylborate, sodium triphenylbutylborate, sodium trianisylbutylborate and ammonium salts such as tetraethylammonium tetraphenylborate.

The most typical examples of a free radical addition polymerizable or crosslinkable compound useful in the present invention is an ethylenically unsaturated compound and, more specifically, a polyethylenically unsaturated compound. These compounds include both monomers having one or more ethylenically unsaturated groups, such as vinyl or allyl groups, and polymers having terminal or pendant ethylenic unsaturation. Such compounds are well known in the art and include acrylic and methacrylic esters of polyhydric alcohols such as trimethylolpropane, pentaerythritol, and the like; and acrylate or methacrylate terminated epoxy resins, acrylate or methacrylate terminated polyesters, etc. Representative examples include ethylene glycol diacrylate, ethylene glycol dimethacrylate, trimethylolpropane triacrylate (TMPTA), pentaerythritol tetraacrylate, pentaerythritol tetramethacrylate, dipentaerythritol hydroxypentacrylate (DPHPA), hexanediol-1,6-dimethacrylate, and diethyleneglycol dimethacrylate.

The cationic dye-borate anion complex is usually used in an amount up to about 1% by weight based on the weight of the photopolymerizable or crosslinkable species in the photohardenable composition. More typically, the cationic dye-borate anion complex is used in an amount of about 0.2% to 0.5% by weight.

While the cationic dye-borate anion complex can be used alone as the initiator, film speeds tend to be quite low and oxygen inhibition is observed. It has been found that it is preferable to use the complex in combination with an autoxidizer. An autoxidizer is a compound which is capable of consuming oxygen in a free radical chain process.

Examples of useful autoxidizers are N,N-dialkylanilines. Examples of preferred N,N-dialkylanilines are dialkylanilines substituted in one or more of the ortho-, meta-, or para- position by the following groups: methyl, ethyl, isopropyl, t-butyl, 3,4-tetramethylene, phenyl, trifluoromethyl, acetyl, ethoxycarbonyl, carboxy, carboxylate, trimethylsilymethyl, trimethylsilyl, triethylsilyl, trimethylgermanyl, triethylgermanyl, trimethylstannyl, triethylstannyl, n-butoxy, n-pentyloxy, phenoxy, hydroxy, acetyl-oxy, methylthio, ethylthio, isopropylthio, thio-(mercapto-), acetylthio, fluoro, chloro, bromo and iodo.

Representative examples of N,N-dialkylanilines useful in the present invention are 4-cyano-N, N-dimethylaniline, 4-acetyl-N,N-dimethylaniline, 4-bromo-N, N-dimethylaniline, ethyl 4-(N,N-dimethylamino) benzoate, 3-chloro-N,N-dimethylaniline, 4-chloro-N,N-dimethylaniline, 3-ethoxy-N,N-dimethylaniline, 4-fluoro-N,N-dimethylaniline, 4-methyl-N,N-dimethylaniline, 4-ethoxy-N,N-dimethylaniline, N,N-dimethylthioanicidine, 4-amino- N,N-dimethylaniline, 3-hydroxy-N,N-dimethylaniline, N,N,N',N'-tetramethyl-1,4-dianiline, 4-acetamido-N, N-dimethylaniline, etc.

Preferred N,N-dialkylanilines are substituted with an alkyl group in the ortho-position and include 2,6-diisopropyl-N,N-dimethylaniline, 2,6-diethyl-N,N-dimethylaniline, N,N,2,4,6-pentamethylaniline (PMA) and p-t-butyl-N,N-dimethylaniline.

The autoxidizers are preferably used in the present invention in concentrations of about 4–5% by weight.

The photohardenable compositions of the present invention can be coated upon a support in a conventional manner and used as a photoresist or in photolithography to form a polymer image; or they can be encapsulated as described in U.S. Pat. Nos. 4,399,209 and 4,440,846 and used to control the release of an image-forming agent. The latter processes typically involve image-wise exposing the photosensitive material to actinic radiation and subjecting the layer of microcapsules to a uniform rupturing force such as pressure, abrasion, or ultrasonic energy.

Several processes can be used to form color images as explained in U.S. application Ser. No. 339,917. If the microcapsules are sensitive to red, green and blue light, images can be formed by direct transmission or reflection imaging or by image processing. Image processing may involve forming color separations (color-seps) corresponding to the red, green and blue component images and sequentially exposing the photosensitive material to three distinct bands of radiation hereinafter designated λ-1, λ-2, and λ-3 sources through each color separation. Otherwise, it may involve electronic processing in which the image or subject to be recorded is viewed through a Dunn or matrix camera and the output from the camera electronically drives three exposure sources corresponding to λ-1, λ-2, and λ-3.

While the discussion herein relates to forming 3-color full color images, 4-color images are also possible. For example, microcapsules containing cyan, magenta, yellow, and black image-forming agents can be provided which have distinct sensitivities at four wavelengths, e.g., λ-1, λ-2, λ-3, and λ-4.

In accordance with the invention, at least one set of the microcapsules in a full color system contains a cationic dye-borate anion complex. The other sets also may contain a cationic dye-borate anion complex, or they may contain a conventional photoinitiator.

In accordance with the preferred embodiments of the invention, a full color imaging system is provided in which the microcapsules are sensitive to red, green, and blue light respectively. The photosensitive composition in at least one and possibly all three microcapsules are sensitized by a cationic dye-borate anion complex. For optimum color balance, the microcapsules are sensitive (λ max) at about 450 nm, 550 nm, and 650 mn, respectively. Such a system is useful with visible light sources in direct transmission or reflection imaing. Such a material is useful in making contact prints or projected prints of color photographic slides. They are also useful in electronic imaging using lasers or pencil light sources of appropriate wavelengths.

Because the cationic dye-borate anion complexes absorb at wavelengths greater than 400 nm, they are colored. Typically, the unexposed dye complex is present with the image-forming agent in the image areas and, thus, the color of the complex must be considered in determining the color of the image. However, the complex is used in very small amounts compared to the image-forming agent and exposure often bleaches the dye complex.

The photohardenable compositions of the present invention can be encapsulated in various wall formers using techniques known in the area of carbonless paper including coacervation, interfacial polymerization, polymerization of one or more monomers in an oil, as well as various melting, dispersing, and cooling methods. To achieve maximum sensitivities, it is important that an encapsulation technique be used which provides high quality capsules which are responsive to changes in the internal phase viscosity in terms of their ability to rupture. Because the borate tends to be acid sensitive, encapsulation procedures conducted at higher pH (e.g., greater than about 6) are preferred.

Oil soluble materials have been encapsulated in hydrophilic wall-forming materials such as gelatin-type materials (see U.S. Pat. Nos. 2,730,456 and 2,800,457 to Green et al) including gum arabic, polyvinyl alcohol, carboxy-methylcellulose; resorcinol-formaldehyde wall formers (see U.S. Pat. No. 3,755,190 to Hart, et al); isocyanate wall-formers (see U.S. Pat. No. 3,914,511 to Vassiliades); isocyanate-polyol wall-formers (see U.S. Pat. No. 3,796,669 to Kirintani et al); urea-formaldehyde wall-formers, particularly urea-resorcinol-formaldehyde in which oleophilicity is enhanced by the addition of resorcinol (see U.S. Pat. Nos. 4,001,140; 4,087,376 and 4,089,802 Foris et al); and melamine-formaldehyde resin and hydroxypropyl cellulose (see commonly assigned U.S. Pat. No. 4,025,455 to Shackle).

Urea-resorcinol-formaldehyde and melamine-formaldehyde capsules with low oxygen permeability are preferred. In some cases to reduce oxygen permeability it is desirable to form a double walled capsule by conducting encapsulation in two stages.

A capsule size should be selected which minimizes light attenuation. The mean diameter of the capsules used in this invention typically ranges from approximately 1 to 25 microns. As a general rule, image resolution improves as the capsule size decreases. If the capsules become too small, they may disappear in the pores or the fiber of the substrate. These very small capsules may therefore be screened from exposure by the substrate. They may also fail to rupture when exposed to pressure or other rupturing means. In view of these problems, it has been determined that a preferred mean capsule diameter range is from approximately 3 to 10 microns. Technically, however, the capsules can range in size up to the point where they become visible to the human eye.

An open phase system may also be used in accordance with the invention instead of an encapsulated one. This can be done by dispersing what would otherwise be the capsule contents throughout the coating on the substrate as discrete droplets. Suitable coatings for this embodiment include polymer binders whose viscosity has been adjusted to match the dispersion required in the coating. Suitable binders are gelatin, polyvinyl alcohol, polyacrylamide, and acrylic lattices. Whenever reference is made to "capsules" and "encapsulation" without reference to a discrete capsule wall in this specification or the appended claims, those terms are intended to include the alternative of an open phase system.

The photosensitive material of the present invention can be used to control the interaction of various image-forming agents.

In one embodiment of the present invention the capsules may contain a benign visible dye in the internal phase in which case images are formed by contacting the exposed imaging material under pressure with a plain paper or a paper treated to enhance its affinity for the visible dye. A benign dye is a colored dye which does not interfere with the imaging photochemistry, for example, by relaxing the excited state of the initiator or detrimentally absorbing or attenuating the exposure radiation.

In preferred embodiment of the invention, images are formed through the reaction of a pair of chromogenic materials such as a color precursor and a color developer, either of which may be encapsulated with the photohardenable composition and function as the image forming agent. In general, these materials include colorless electron donating type compounds and are well known in the art. Representative examples of such color formers include substantially colorless compounds having in their partial skeleton a lactone, a lactam, a sultone, a spiropyran, an ester or an amido structure such as triarylmethane compounds, bisphenylmethane compounds, xanthene compounds, fluorans, thiazine compounds, spiropyran compounds and the like. Crystal Violet Lactone and Copikem X, IV and XI are often used. The color formers can be used alone or in combination.

The developer materials conventionally employed in carbonless paper technology are also useful in the present invention. Illustrative examples are clay minerals such as acid clay, active clay, attapulgite, etc.; organic acids such as tannic acid, gallic acid, propyl gallate, etc.; acid polymers such as phenol-formaldehyde resins, phenol acetylene condensation resins, condensates between an organic carboxylic acid having at least one hydroxy group and formaldehyde, etc.; metal salts or aromatic carboxylic acids such as zinc salicylate, tin salicylate, zinc 2-hydroxy naphthoate, zinc 3,5 di-tert butyl salicylate, zinc 3,5-di-(α-methylbenzyl)salicylate, oil soluble metal salts or phenol-formaldehyde novolak resins (e.g., see U.S. Pat. Nos. 3,672,935; 3,732,120 and 3,737,410)

such as zinc modified oil soluble phenol-formaldehyde resin as disclosed in U.S Pat. No. 3,732,120, zinc carbonate etc. and mixtures thereof.

As indicated in U.S. Pat. Nos. 4,399,209 and 4,440,846, the developer may be present on the photosensitive sheet (providing a so-called self-contained system) or on a separate developer sheet.

In self-contained systems, the developer may be provided in a single layer underlying the microcapsules as disclosed in U.S. Pat. No. 4,440,846. Alternatively, the color former and the color developer may be individually encapsulated in photosensitive capsules and upon exposure botn capsule sets image-wise rupture releasing color former and developer which mix to form the image. Alternatively, the developer can be encapsulated in non-photosensitive capsules such that upon processing all developer capsules rupture and release developer but the color former containing capsules rupture in only the unexposed or underexposed area which are the only areas where the color former and developer mix. Still another alternative is to encapsulate the developer in photosensitive capsules and the color former in non-photosensitive capsules.

The present invention is not necessarily limited to embodiments where the image-forming agent is present in the internal phase. Rather, this agent may be present in the capsule wall of a discrete capsule or in the binder of an open phase system or in a binder or coating used in combination with discrete capsules or an open phase system designed such that the image-wise ruptured capsules release a solvent for the image-forming agent. Embodiments are also envisioned in which a dye or chromogenic material is fixed in a capsule wall or binder and is released by inter-action with the internal phase upon rupturing the capsules.

The most common substrate for this invention is paper. The paper may be a commercial impact raw stock, or special grade paper such as cast-coated paper or chromerolled paper. The latter two papers are preferred when using capsules having a diameter between approximately 1 and 5 microns, because the surface of these papers is smoother and therefore the capsules are not as easily embedded in the stock fibers. Transparent substrates such as polyethylene terephthalate and translucent substrates can also be used in this invention. Their advantage is that the latent image formed need not be reversed for printing.

Syntnesis Examples 1 and 2 respectively illustrate the preparation of borates and dye-borate complexes.

SYNTHESIS EXAMPLE 1

Dissolve triphenylborane in 150 ml of dry benzene (1M) under nitrogen atmosphere. Place flask in a cool water bath and, while stirring, add n-BuLi, (1.1 e.g.) via syringe. A white precipitate soon formed after addition was started. Stirring is continued about 45-60 min. Dilute with 100 ml hexane and filter, washing with hexane. This resultant Li salt is slightly air unstable. Dissolve the white powder in about 200 ml distilled water and, with vigorous stirring, add aqueous solution of tetramethyl ammonium chloride (1.2 e.g. of theoretical in 200 ml). A thick white precipitate forms. Stir this aqueous mixture about 30 min. at room temperature, then filter. Wash collected white solid with distilled water.

As an alternative synthesis, to a 1.0M solution of 2.0 equivalents of 1-butene in dry, oxygen-free dichloromethane, under inert atomosphere, was added slowly dropwise with stirring, 1.0 equivalents of a 1.0M solution of dibromethane-methylsulfide complex in dichloromethane. The reaction mixture stirred at reflux for 36 hours and the dichloromethane and excess 1-butene were removed by simple distillation. Vacuum distillation of the residue afforded 0.95 equivalents of a colorless mobile oil (Bp 66-7 0.35 mm Hg, "BNMR;bs (4.83PPM). Under inert atmosphere, this oil was dissolved in dry, oxygen-free tetrahydrofuran to give a 1.0M solution ano 3.0 equivalents of a 2.0M solution of pnenylmagnesium chloride in tetrahydrofuran were added dropwise with stirring. After stirring 16 hours, the resultant solution was added slowly with vigorous stirring to 2 equivalents of tetramethylammonium chloride, as a 0.2M solution, in water. The resulting white flocculate solid was filtered and dried to afford a near quantitative amount of the desired product Mp 250°-2° C., "BNMR;bs (-3.70 PPM).

SYNTHESIS EXAMPLE 2

Sonicate a suspension of a borate salt (1 g/10 ml) in MeOH, to make a very fine suspension. Protect flask from light by wrapping with aluminum foil then add 1 equivalent of dye. Stir this solution with low heat on a hot plate for about 30 min. Let cool to room temperature then dilute with 5-10 volumes of ice water. Filter the resultant solid and wash with water until washings are colorless. Suction filter to dryness. Completely dry initiator complex by low heat (about 50° C.) in a vacuum drying oven. Initiator is usually formed quantitatively. Analysis by H-NMR indicates 1:1 complex formation typically greater than 90%.

The present invention is illustrated in more detail by the following non-limiting Examples.

EXAMPLE 1

Capsule Preparation

1. Into a 600 ml stainless steel beaker, 104 g water and 24.8 g isobutylene maleic anhydride copolymer (18%) are weighed.

2. The beaker is clamped in place on a hot plate under an overhead mixer. A six-bladed, 45° pitch, turbine impeller is used on the mixer. 3. After thoroughly mixing, 3.1 g pectin (polygalacturonic acid methyl ester) is slowly sifted into the beaker. This mixture is stirred for 20 minutes.

4. The pH is adjusted to 4.0 using a 20% solution of $H_2SO_4$, and 0.1 g Quadrol (2-hydroxypropyl ethylenediamine with propylene oxide from BASF) is added.

5. The mixer is turned up to 3000 rpm and the internal phase is added over a period of 10-15 seconds. Emulsification is continued for 10 minutes.

6. At the start of emulsification, the hot plate is turned up so heating continues during emulsification.

7. After 10 minutes, the mixing speed is reduced to 2000 rpm and 14.1 g urea solution (50% w/w), 3.2 g resorcinol in 5 g water, 21.4 g formaldehyde (37%), and 0.6 g ammonium sulfate in 10 ml water are added at two-minute intervals.

8. The beaker is covered with foil and a heat gun is used to help bring the temperature of the preparation to 65° C. When 65° C. is reached, the hot plate is adjusted to maintain this temperature for a two to three hour cure time during which the capsule walls are formed.

9. After curing, the heat is turned off and the pH is adjusted to 9.0 using a 20% NaOH solution.

10. Dry sodium bisulfite (2.8 g) is added and the capsule preparation is cooled to room temperature.

Three batches of microcapsules were prepared for use in a full color imaging sheet using the three internal phase compositions set forth below. Internal Phase A provides a yellow image-forming agent and is sensitive at 420 nm, Phase B provides a magenta image-forming agent and is sensitive at 480 nm, and Phase C contains a cyan image-forming agent and a cationic dye-borate anion complex which is sensitive at 570 nm. The three batches of microcapsules were mixed, coated on a support, and dried to provide a full color imaging sheet.

| Internal Phase A (420 nm) | |
| --- | --- |
| TMPTA | 35 g |
| DPHPA | 15 g |
| 3-thenoyl-7-diethylamino coumarin | 15 g |
| 2-Mercaptobenzoxazole (MBO) | 2.0 g |
| Pentamethylaniline (PMA) | 1.0 g |
| Reakt Yellow (BASF) | 5.0 g |
| SF-50 (Union Carbide Isocyanate) | 1.67 g |
| N-100 (Desmodur Polyisocyanate Resin) | 3.33 g |
| Internal Phase B (480 nm) | |
| TMPTA | 35 g |
| DPHPA | 15 g |
| 9-(4'-isopropylcinnamoyl)-1,2,4,5,-tetrahydro-3H, 6H, 10H[1]-benzopyrano[9, 9A,1-yl]quinolazine-10-one | 0.15 g |
| MBO | 1.0 g |
| PMA | 2.0 g |
| Magenta Color Former (HD-5100 Hilton Davis Chemical Co.) | 8.0 g |
| SF-50 | 1.67 g |
| N-100 | 3.33 g |
| Internal Phase C (570 nm) | |
| TMPTA | 50 g |
| Cationic Dye Complex No. 2 | 0.15 g |
| PMA | 2.0 g |
| Cyan Color Former (S-29663 Hilton Davis Chemical Co.) | 4.0 g |
| SF-50 | 1.67 g |
| N-100 | 3.33 g |

EXAMPLE 2

Capsule Preparation

1. Into a 600 ml stainless steel beaker, 110 g water and 4.6 g isobutylene maleic anhydride copolymer (dry) are weighed 2. The beaker is clamped in place on a hot plate under an overhead mixer. A six-bladed, 45° pitch, turbine impeller is used on the mixer.

3. After thoroughly mixing, 4.0 g pectin (polygalacturonic acid methyl ester) is slowly sifted into the beaker. This mixture is stirred for 2 hours at room temperature (800–1200 rpm).

4. The pH is adjusted to 7.0 with 20% sulfuric acid.

5. The mixer is turned up to 3000 rpm and the internal phase is added over a period of 10–15 seconds. Emulsification is continued for 10 minutes. Magenta and yellow precursor phases are emulsified at 25°–30° C. Cyan phase is emulsified at 45°–50° C. (oil), 25°–30° C. (water).

6. At the start of emulsification, the hot plate is turned up so heating continues during emulsification.

7. After 10 minutes, the pH is adjusted to 8.25 with 20% sodium carbonate, the mixing speed is reduced to 2000 rpm, and a solution of melamine-formaldehyde prepolymer is slowly added which is prepared by dispersing 3.9 g melamine in 44 g water, adding 6.5 g formaldehyde solution (37%) and heating at 60° C. until the solution clears plus 30 minutes. 8. The pH is adjusted to 6.0, the beaker is covered with foil and placed in a water bath to bring the temperature of the preparation to 65° C. When 65° C. is reached, the hot plate is adjusted to maintain this temperature for a two hour cure time during which the capsule walls are formed.

9. After curing, mixing speed is reduced to 600 rpm, formaldehyude scanvenger solution (7.7 g urea and 7.0 g water) is added and the solution was cured another 40 minutes.

10. The pH is adjusted to 9.5 using a 20% NaOH solution and stirred overnight at room temperature.

Three batches of microcapsules were prepared as above for use in a full color imaging sheet using the three internal phase compositions set forth below.

| Yellow Forming Capsules (420 nm) | |
| --- | --- |
| TMPTA | 35 g |
| DPHPA | 15 g |
| 3-thenoyl-7-diethylamino coumarin | 15 g |
| 2-Mercaptobenzoxazole (MBO) | 2.0 g |
| 2,6-Diisopropylaniline | 1.0 g |
| Reakt Yellow (BASF) | 5.0 g |
| N-100 (Desmodur Polyisocyanate Resin) | 3.33 g |
| Magenta Forming Capsules (550 nm) | |
| TMPTA | 50 g |
| Complex 8A | 0.2 g |
| 2,6-Diisopropylaniline | 2.0 g |
| HD5100 (Magenta color precursor from Hilton-Davis Chemical Co.) | 12.0 g |
| Cyan Forming Capsules (650 nm) | |
| TMPTA | 50 g |
| Complex 11 H | 0.31 g |
| 2,6-diisopropylaniline | 2.0 g |
| Cyan Precursor (CP-177 of Hilton-Davis Chemical Co.) | 6 g |

The three batches of microcapsules were blended together and coated on a support to provide an imaging material in accordance with the present invention.

Having described the invention in detail and by reference to preferred embodiments thereof, it will be apparent that modifications and variations are possible without departing from the scope of the invention defined in the appended claims

What is claimed is:

1. A photohardenable composition comprising a free radical addition polymerizable or crosslinkable compound and a cationic dye-borate anion complex, said complex being capable of absorbing actinic radiation and producing free radicals which initiate free radical polymerization or crosslinking of said compound.

2. The photohardenable composition of claim 1 wherein said cationic dye-borate anion complex is represented by the formula (I):

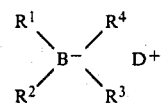

where D is a cationic dye moiety; and $R^1$, $R^2$, $R^3$ and $R^4$ are the same or different and selected from the group consisting of alkyl, aryl, aralkyl, alkaryl, alkenyl, alkynyl, alicyclic, heterocyclic, and allyl groups.

3. The photohardenable composition of claim 2 wherein said cationic dye is selected from the group consisting of cationic methine, polymethine, triarylmethane, indoline, azine, thiazine, xanthene, oxazine, and acridine dyes.

4. The photohardenable composition of claim 3 wherein said cationic dye is selected from the group consisting of cationic cyanine, carbocyanine, hemicyanine, rhodamine, and azamethine dyes.

5. The photohardenable composition of claim 4 wherein said compound is an ethylenically unsaturated compound.

6. The photohardenable composition of claim 5 wherein at least one of $R^1$, $R^2$, $R^3$ and $R^4$ is an alkyl group.

7. A photosensitive material comprising a support having a layer of a photohardenable composition on the surface thereof, said composition comprising a free radical addition polymerizable or crosslinkable compound and a cationic dye-borate anion complex, said complex being capable of absorbing actinic radiation and producing free radicals which initiate free radical polymerization or crosslinking of said compound.

8. The photosensitive material of claim 7 wherein said cationic dye-borate anion complex is represented by the formula (I)

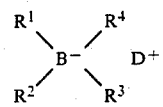

where D is a cationic dye moiety; and $R^1$, $R^2$, $R^3$ and $R^4$ are the same or different and selected from the group consisting of alkyl, aryl, aralkyl, alkaryl, alkenyl, alkynyl, alicyclic, heterocyclic, and allyl groups.

9. The photosensitive material of claim 8 wherein said cationic dye is selected from the group consisting of cationic methine, polymethine, triarylmethane, indoline, azine, thiazine, xanthene, oxazine, and acridine dyes.

10. The photosensitive material of claim 8 wherein said cationic dye is selected from the group consisting of cationic cyanine, carbocyanine, hemicyanine, rhodamine, and azamethine dyes.

11. The photosensitive material of claim 10 wherein said compound is an ethylenically unsaturated compound.

12. The photosensitive material of claim 11 wherein at least one of $R^1$, $R^2$, $R^3$ and $R^4$ is an alkyl group and at least one is an aryl group.

* * * * *